(12) United States Patent
Akitsu et al.

(10) Patent No.: US 9,016,595 B2
(45) Date of Patent: *Apr. 28, 2015

(54) LIQUID SPRAYER

(76) Inventors: Hiromi Akitsu, Yamashina Ku (JP);
Shiang Aling Shiu Shu, Taipei (TW);
Christian Dinner, Préverenges (CH);
Jerry Ping Hsin Chu, Taipei (TW)

(*) Notice: Subject to any disclaimer, the term of this patent is extended or adjusted under 35 U.S.C. 154(b) by 308 days.

This patent is subject to a terminal disclaimer.

(21) Appl. No.: 13/619,831

(22) Filed: Sep. 14, 2012

(65) Prior Publication Data

US 2013/0292492 A1 Nov. 7, 2013

(30) Foreign Application Priority Data

May 7, 2012 (JP) .................................. 2012-106349

(51) Int. Cl.
| | |
|---|---|
| B05B 17/06 | (2006.01) |
| B05B 17/00 | (2006.01) |
| B05B 15/00 | (2006.01) |
| A61L 9/14 | (2006.01) |
| B05B 15/06 | (2006.01) |

(52) U.S. Cl.
CPC ........... B05B 17/0684 (2013.01); B05B 15/005 (2013.01); A61L 2209/132 (2013.01); B05B 17/0646 (2013.01); A61L 9/14 (2013.01); B05B 15/065 (2013.01)

(58) Field of Classification Search
CPC   B05B 15/005; B05B 15/065; B05B 17/0646; B05B 17/0684; A61L 9/14; A61L 2209/132

USPC ............ 239/4, 102.1, 102.2, 67, 69–71, 288, 239/302, 326, 331, 338; 422/20, 120; 128/200.14, 200.16

See application file for complete search history.

(56) References Cited

U.S. PATENT DOCUMENTS

| | | | | |
|---|---|---|---|---|
| 4,301,093 | A * | 11/1981 | Eck ..................................... | 261/1 |
| 6,550,472 | B2 * | 4/2003 | Litherland et al. ........ | 128/200.18 |
| 2007/0235555 | A1 * | 10/2007 | Helf et al. ................... | 239/102.2 |
| 2008/0011875 | A1 * | 1/2008 | Sipinski et al. ............ | 239/102.2 |
| 2009/0065600 | A1 * | 3/2009 | Tranchant et al. ................. | 239/4 |
| 2009/0114737 | A1 * | 5/2009 | Yu et al. .......................... | 239/69 |
| 2011/0011948 | A1 * | 1/2011 | Huang ............................ | 239/44 |

FOREIGN PATENT DOCUMENTS

| | | |
|---|---|---|
| JP | 2007203225 A | 8/2007 |
| JP | 2007203226 A | 8/2007 |

(Continued)

*Primary Examiner* — Darren W Gorman
(74) *Attorney, Agent, or Firm* — Laura M. Lloyd; Leech Tishman Fuscaldo & Lampl (57) ABSTRACT

A transducer type liquid sprayer in which a storage tank for storing spray liquid can be easily replaced together with a core for soaking up the spray liquid from the storage tank is provided. The liquid sprayer includes a spray liquid storage unit and a main body for supporting the spray liquid storage unit and a power supply unit. The spray liquid storage unit includes a core for soaking up spray liquid and the main body includes a lid member attached to a support member for supporting the spray liquid storage unit so that the lid member can be opened and closed. A spray hole is formed in the lid member and a transducer is also disposed inside the lid member and electrically connected to the power supply unit. The transducer disposed inside the lid member is in close contact with and pressed against the core.

4 Claims, 8 Drawing Sheets

(56) References Cited

FOREIGN PATENT DOCUMENTS

| | | |
|---|---|---|
| JP | 2010007899 A | 1/2010 |
| JP | 2010119562 A | 6/2010 |
| WO | 00/51747 A1 | 9/2000 |
| WO | 02/09888 A1 | 2/2002 |
| WO | 03/066115 A2 | 8/2003 |
| WO | 03/099458 A2 | 12/2003 |
| WO | 2004/043502 A1 | 5/2004 |
| WO | 2004/048002 A1 | 6/2004 |
| WO | 2004/056492 A1 | 7/2004 |
| WO | 2006/004891 A1 | 1/2006 |
| WO | 2006/004902 A1 | 1/2006 |
| WO | 2006/110794 A1 | 10/2006 |
| WO | 2008/103238 A1 | 8/2008 |
| WO | 2010/021716 A1 | 2/2010 |

* cited by examiner

LIQUID SPRAYER

CROSS-REFERENCE TO RELATED APPLICATIONS

This Application is a continuation-in-part and claims the benefit of Japanese Patent Application Number 2012-106349, filed May 7, 2012, the contents of which is incorporated herein by reference in entirety.

BACKGROUND

As is known in the art, there are conventional spray cans using propellants as liquid sprayers for spraying liquid fragrance or the like. This spray can type liquid sprayer has safety issues because of the use of flammable gas as a propellant. Therefore, in recent years, transducer type liquid sprayers for spraying liquid fragrance have been developed which use transducers for generating ultrasonic vibration.

Liquid sprayers using a transducer, as disclosed in JP 2010-7899 A, include a liquid storage tank for storing spray liquid, a mist producing means for turning the spray liquid into mist, and a spray liquid supply means for supplying the spray liquid in the liquid storage tank to the mist producing means. The spray liquid supply means includes a first liquid retaining body having one end disposed at a predetermined position in the liquid storage tank to absorb the spray liquid in the liquid storage tank, a substantially cylindrical second liquid retaining body brought into contact with the other end of the first liquid retaining body and having a predetermined inside diameter and a predetermined outside diameter, and a third liquid retaining body having one end brought into contact with an outer peripheral face of the second liquid retaining body at predetermined contact pressure and the other end brought into contact with the mist producing means at predetermined contact pressure.

In the sprayer disclosed in JP 2010-7899 A, however, the liquid storage tank for storing the spray liquid is detached from the liquid retaining body for absorbing the spray liquid in the liquid storage tank and only the liquid storage tank is attached and detached to add the spray liquid. Therefore, if the sprayer is used for a long term, solid components and impurities included in the spray liquid accumulate in the liquid retaining body and the liquid retaining body cannot soak up the spray liquid. Moreover, the liquid retaining body is housed in an L-shaped casing and therefore the liquid retaining body is difficult to detach from the casing and is not easy to replace.

Further, at least some prior art liquid sprayers have the spray liquid and spray hole positioned such that the spray mist is sprayed in an upward vertical direction, precluding wall mounting high on the wall, as the spray mist will be sprayed onto the ceiling. Further, in these types of sprayers, if they are placed lower to the ground, the mist can become an eye or nasal irritant if it is dissipated in close proximity to someone nearby.

SUMMARY

Therefore, an object of the invention is to achieve a transducer type liquid sprayer in which a storage tank for storing spray liquid can be easily replaced together with a core for soaking up the spray liquid from the storage tank. In addition, the liquid sprayer has a horizontally directed spray mist, such that the sprayer may be mounted on a wall.

To realize the object, the present inventor repeatedly carried out test production and experiments to achieve the invention described herein. As a result, the inventor has found a notable fact that a transducer may be mounted on a front facing lid, and when the lid and transducer are detached from the core, a spray liquid storage unit can be easily attached and detached.

According to the present invention, a liquid sprayer for dispensing a spray liquid is provided which achieves the above described objectives. The liquid sprayer comprises a main body having a support member having a back face, an upper portion, and a lower portion, and a power supply unit positioned in the interior of the support member, on the upper portion of the support member. A lid member having a front face is rotatably connected to the support member. When the lid member is positioned in an open position, the upper portion and lower portion of the support member are revealed. When the lid member is positioned in the closed position, the lid member closes down on the support member, forming the main body. The lid member also has a a spray hole formed on the front face of the lid member. A spray liquid storage unit is supported by and positioned on the lower portion of the support member, the spray liquid storage unit has a spray liquid housed in a storage tank and a core for soaking up spray liquid. The spray liquid storage unit is removable from the main body when the lid member is in the open position. A transducer is disposed inside the lid member and electrically connected to the power supply unit, such that when the lid member is in the closed position, the transducer is in close contact with an pressed against a section of the core. The core, transducer and spray hole are substantially aligned, such that when electric power is supplied from the power supply unit to the transducer, the spray liquid retained in the core is turned into a spray mist by vibration of the transducer and sprayed outside the main body through the spray hole.

Preferably, when the lid member is in an open position, the upper portion and lower portion of the support member are revealed, and when the lid member is in a closed position, the transducer is disposed parallel to a front face of the core. In this position, the core, transducer and spray hole will be substantially aligned to dispense the spray liquid in a spray mist upon the application of power to the transducer.

In other embodiments, the lid member has side faces rising from opposite sides of the front face of the lid member such that the lid and support member form a shell which makes up the main body. More preferably, a support arm is positioned between opposite side faces of the lid member and the transducer is affixed to the support arm, which raises and lowers the transducer with lid member and aligns the transducer with the spray hole and core. The liquid sprayer may also have one or more support members for supporting one or both of the power supply unit and the spray liquid storage unit.

According a preferred embodiment, the spray hole is formed in the lid member so as to face a front face of the core when the lid member is closed onto the support member. The transducer faces the spray hole and is disposed inside the lid member. The transducer is in close contact with and pressed against the front face of the core and is supported by the support member when the lid member is closed onto the support member. Therefore, the transducer is detached from the core when the lid member is opened and the spray liquid storage unit supported on the support member can be easily attached and detached.

BRIEF DESCRIPTION OF THE DRAWINGS

FIG. 1 is a perspective view showing an outward appearance of the liquid sprayer according to one embodiment of the invention;

DESCRIPTION

Figure 1:
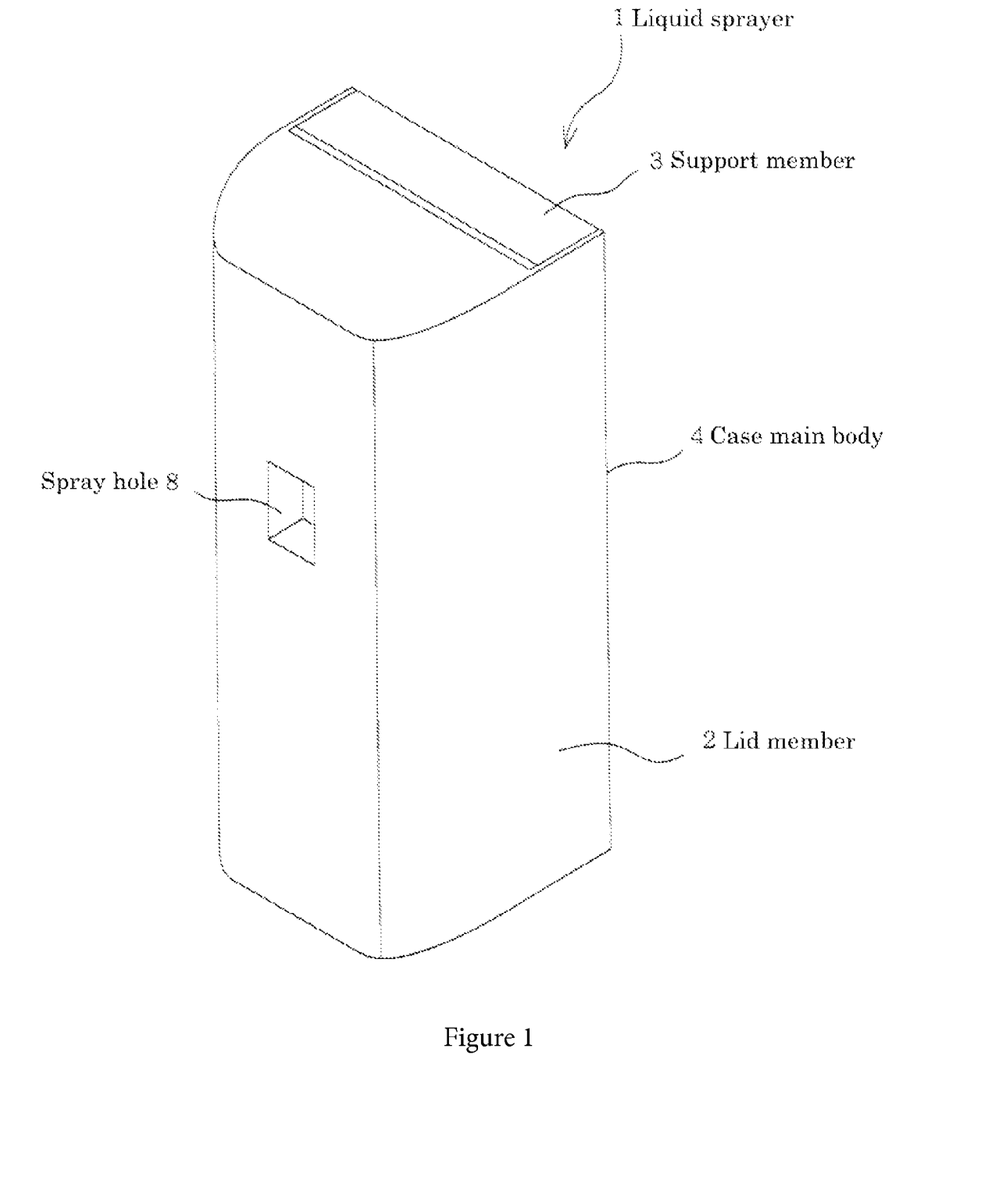

Referring now to FIG. 1, a liquid sprayer 1 according to one embodiment of the invention is shown. As shown in FIG. 1, a liquid sprayer 1 comprises a case main body 4 (main body) having a lid member 2 that forms a front face side and a support member 3 forming a back face side of the main body.

Figure 2:
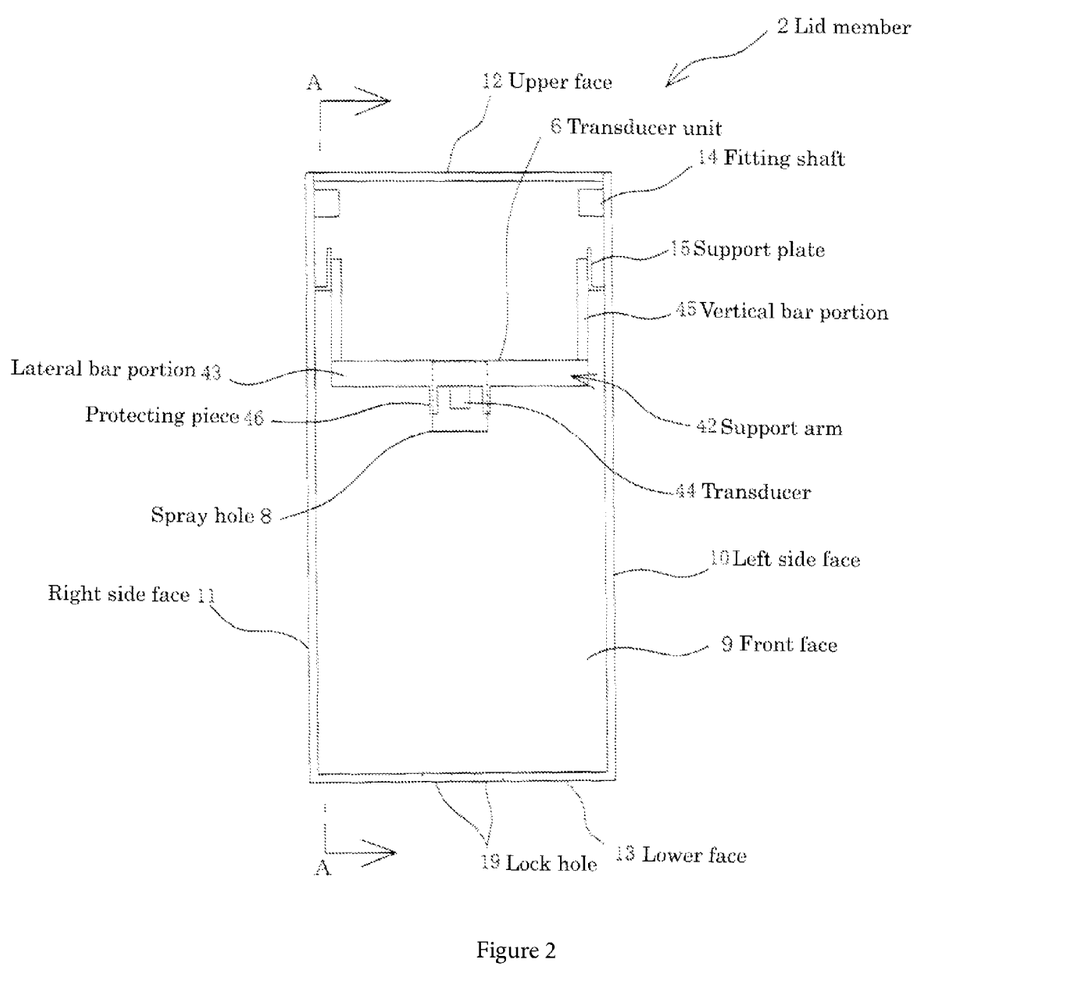
FIG. 2 is a front view of an inside of a lid member of the liquid sprayer shown in FIG. 1.
Figure 3:
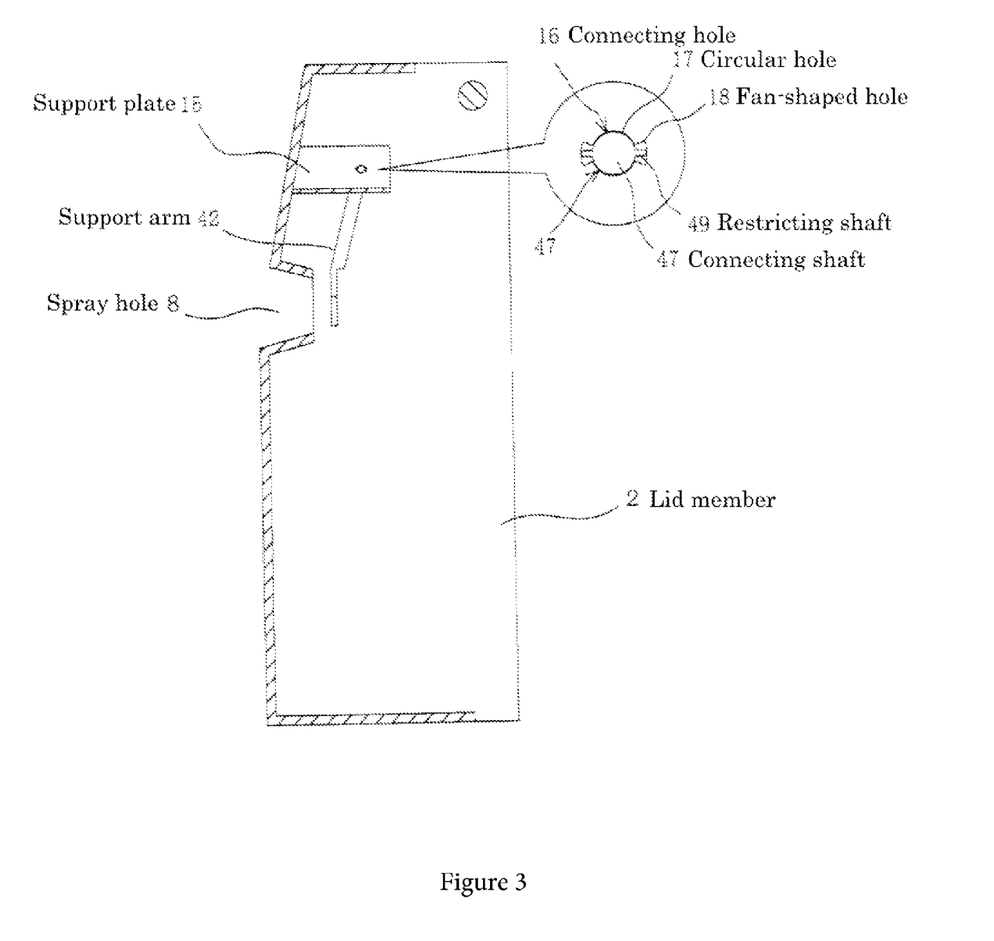
FIG. 3 is a sectional view showing a section of the lid member shown in FIG. 2 and taken along line A-A.

Referring now to FIG. 2 and FIG. 3, FIG. 2 is a front view of the inside of the lid member 2 of the liquid sprayer 1 (shown in FIG. 1), and FIG. 3 is a sectional view showing a section of the lid member shown in FIG. 2 and taken along line A-A. As shown in FIGS. 2 and 3, the case main body 4 houses spray liquid storage unit 5, which stores spray liquid, a transducer unit 6, and a power supply unit 7. The transducer unit 6 turns the spray liquid stored in the spray liquid storage unit 5 into mist, and the power supply unit 7 supplies electric power to the transducer unit 6.

As shown in FIG. 1 and FIG. 2, the lid member 2 is formed by left and right side faces 10 and 11 and upper and lower faces 12 and 13. In some embodiments, the upper and lower faces 12 and 13 extend backward in a rising manner from the front face 9 at a substantially central portion thereof. A spray hole 8 for discharging the spray liquid which has been turned into the mist by the transducer unit 6 is positioned between the left and right side faces 10 and 11. Preferably, the spray hole 8 is positioned closer to the upper face 12 than the lower face 13, but in other embodiments, the spray hole 8 is centrally located. In some embodiments, the back face of the support member may have impressions or grooves for wall mounting.

In another embodiment (not shown), the main body of the liquid sprayer comprises a power indicator display electrically connected to the power supply unit 7 for indicating to a user if additional power is needed to supply the unit (e.g., batteries). In another embodiment (not shown) the main body of the liquid sprayer comprises a light sensor, motion detector, or other means for for automatic turn off or turn on of the device.

In one embodiment, one or more fitting shafts 14 are positioned on the inner sides of the left and right side faces 10 and 11. The fitting shafts 14 are connected to the support member 3, and protrude to face each other from back upper end portions and support plates 15a and 15b. The support plates 15a and 15b support the transducer unit 6 and are positioned to face each other at positions above the spray hole 8.

Referring again to FIG. 3, a sectional view of a section of the lid member 2 shown in FIG. 2, taken along line A-A is shown. Also shown in FIG. 3 is an expanded view of the support plates 15a and 15b. Positioned on each of support plates 15a and 15b are a connecting shaft 47 and a restricting shaft 49, as well as a connecting hole 16 which is formed by a circular hole 17 and a pair of fan-shaped holes 18. Fan-shaped holes 18 extend from the circular hole 17 to be symmetric with respect to a point from the circular hole 17 (see an enlarged view of the connecting hole 16 shown in FIG. 3). Referring again to FIG. 2, an optional pair of lock holes 19 are positioned in the lower face 13.

Figure 4:
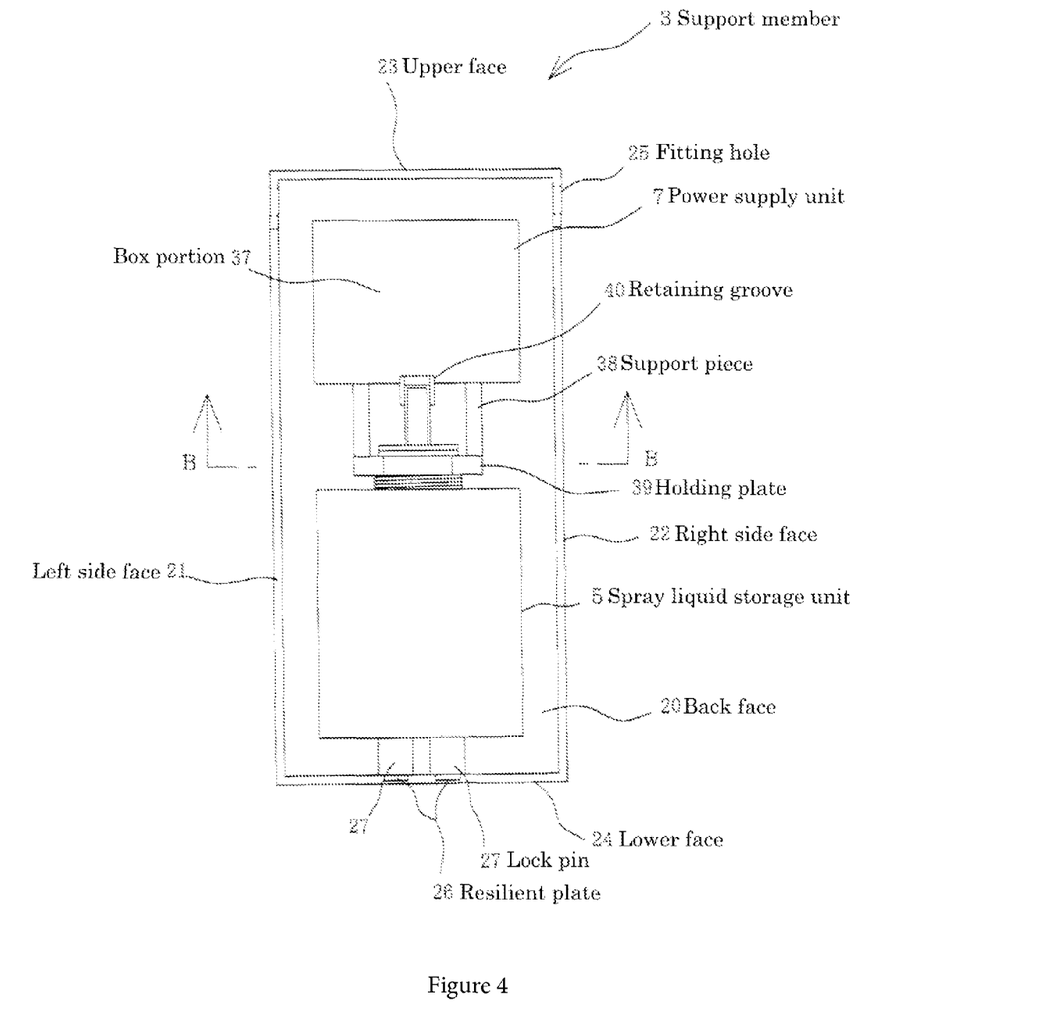
FIG. 4 is a front view showing an inside of a support member of the liquid sprayer shown in FIG. 1.
Figure 5:
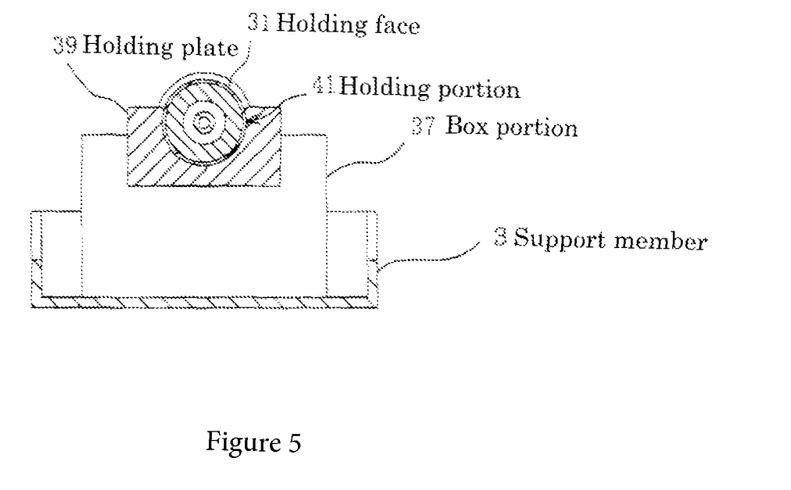
FIG. 5 is a sectional view showing a section of the support member shown in FIG. 4 and taken along line B-B.

As shown in FIGS. 4 and 5, the support member 3 is formed by left and right side faces 21 and 22 and upper and lower faces 23 and 24 extending forward in rising manners from a back face 20 disposed to be sandwiched between the opposite side faces of the lid member 2. The upper face 12 of the lid member 2 and the upper face 23 of the support member 3 form an upper face of the case main body 4 and the lower face 13 of the lid member 2 and the lower face 24 of the support member 3 form the lower face of the case main body 4. Fitting holes 25, 25 in which the fitting shafts 14, 14 of the lid member 2 are to be fitted are formed in upper end portions of the left and right side faces 21 and 22. Therefore, the lid member 2 is connected to the support member 3 to be able to turn by using the fitting shafts 14, 14 fitted in the fitting holes 25, 25 in the support member 3 as rotary shafts.

Figure 6:
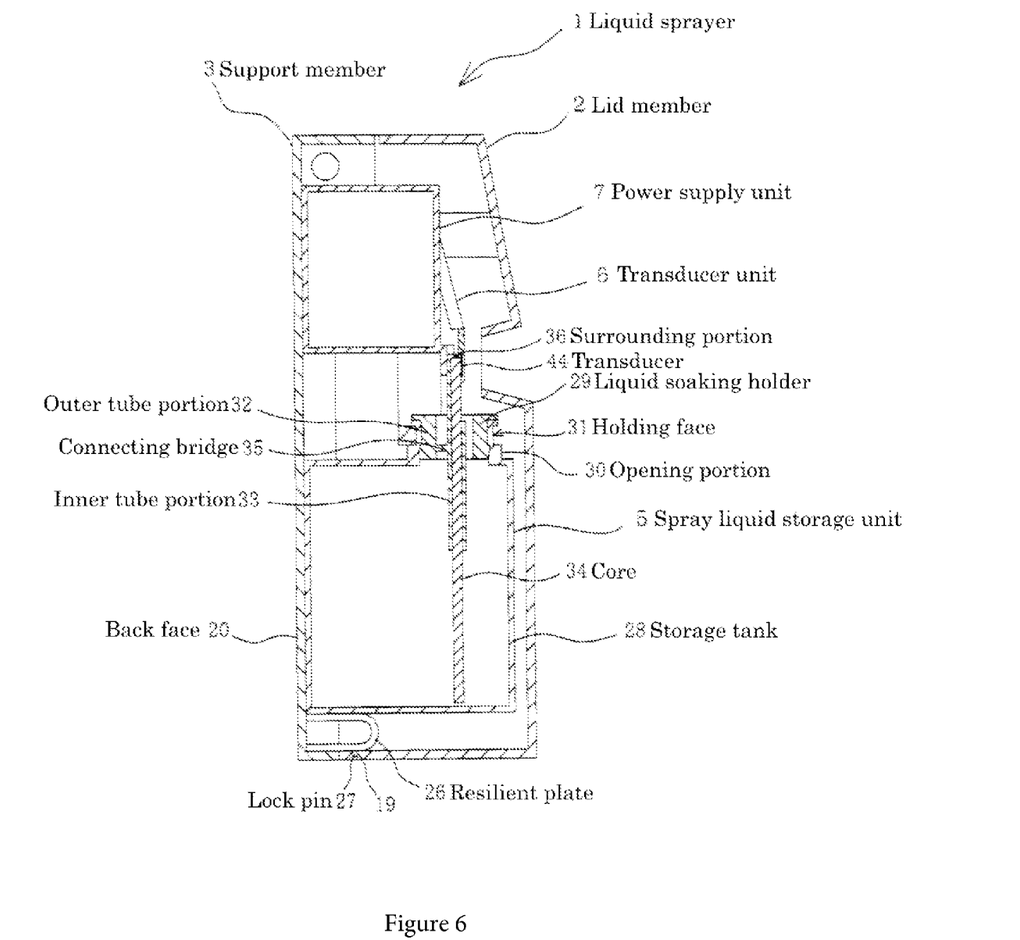
FIG. 6 is a sectional view showing a central vertical sectional view of the liquid sprayer shown in FIG. 1.

Inside the support member 3, the power supply unit 7 is fixed to an upper portion of the support member 3 and the spray liquid storage unit 5 is disposed at a lower portion of the support member 3. As shown in FIG. 6, at a lower end portion in the support member 3, resilient plates 26 having U shapes in a side view protrude forward with their only upper ends fixed to the back face 20 and lock pins 27 protruding downward from the resilient plates 26 can move in a vertical direction as the resilient plates 26 bend. In this way, when the lid member 2 is closed onto the support member 3, the lock pins 27 of the support member 3 are fitted in the lock holes 19, 19 in the lid member 2 to lock opening and closing of the lid member 2 with respect to the support member 3.

As shown in FIGS. 4 and 6, the spray liquid storage unit 5 is formed by a storage tank 28 which stores the spray liquid and a core 34 for soaking up the spray liquid from the storage tank 28. The storage tank may be made from suitable materials for holding spray liquids such as polymers and glass. Preferred materials are recyclable.

In some embodiments, the storage tank 28 has an opening portion 30, into which a liquid soaking holder 29 is inserted, in its upper face. The liquid soaking holder 29 is preferably made from a somewhat rigid material that can support the core 34. An outer side face of the opening portion 30 has a base end formed in a shape of a thread groove and a tip end having a large diameter. Between the thread-shaped portion and the large-diameter portion, a holding face 31 having a smaller diameter than both the portions is formed.

The liquid soaking holder 29 may include an outer tube portion 32 fitted and fixed into the opening portion 30 in the storage tank 28 and an inner tube portion 33 inserted through a hollow portion in the outer tube portion 32 and extending from an inside to an outside of the storage tank 28 and the core 34, for soaking up the spray liquid in the storage tank 28 by capillary action, is fixed in a hollow portion of the inner tube portion 33. The remaining portions of the liquid soaking holder 29 which are parts of the outer tube portion 32 and the inner tube portion 33 are connected by a connecting bridge 35 and a surplus of the spray liquid soaked up by the core 34 returns into the storage tank 28 from a portion between both the tube portions 32 and 33 which are not connected by the connecting bridge 35. A front face of a tip end portion of the inner tube portion 33 may be notched to expose the core 34 and respective wall faces of the tip end portion of the inner tube portion 33 and brought into contact with left and right side faces, a back face, and an upper face of the core 34 form a surrounding portion 36.

In other embodiments, a cap (not shown), such as a screw cap, may be fitted onto the a thread groove formed at the opening portion 30 of the storage tank 28. The cap aids in preventing evaporation of the spray liquid from the storage tank 28.

The core 34 may be formed to have a rectangular section. Preferably, the core 34 is formed from a material that has the ability to flow liquid, particularly without assistance and in opposition to gravity, such as by capillary action. The material for core 34, may be felt, nonwoven fabric made of natural pulp, and material obtained by twining fibers such as polypropylene and polyethylene may be used. In a preferred embodiment, the core is a 0.240 g/cc wick, made of HRM, which is 120 mm length×7 mm diameter.

As shown in FIGS. 4 to 6, the power supply unit 7 includes a box portion 37 for housing a battery and a control board. The support member 3 may also have a holding plate 39 supported by a pair of support pieces 38, 38 extending downward from the box portion 37, and a retaining groove 40 provided to a front face of the box portion 37. In some embodiments, the box portion 37 may contain a key pad for setting automatic spray intervals. The key pad may be a buttons or an electronic display, such as an LED display with programmable settings, such a from 1 to 5 second intervals, preferably 2 second intervals every 15 or 30 minutes, etc., or a manual setting, as may be desired by the user.

As shown in FIG. 5, a C-shaped holding portion 41 which is open forward may be formed in the holding plate 39 and the holding portion 41 has such an inside diameter as to be fitted over the holding face 31 of the storage tank 28. When the holding portion 41 of the power supply unit 7 holds the holding face 31 of the storage tank 28, the surrounding portion 36 of the inner tube portion 33 extends upward from the opening portion 30 of the storage tank 28 and is fitted in the retaining groove 40.

As power-supply voltage of the power supply unit 7, DC 4.5 V, 6.0 V, and 7.5 V may be used, by way of example.

Referring again to FIGS. 2 and 3, the transducer unit 6 may include a support arm 42 having a recessed shape and a transducer 44 may be fixed to a lateral bar portion 43 of the support arm 42, and vertical bar portions 45a and 45b. The support arm 42 extends between vertical bar portions 45a and 45b, while tilting, from the lateral bar portion 43. The lateral bar portion 43 is provided with two protecting pieces 46a and 46b. The protecting pieces 46a and 46b are positioned parallel on opposite sides of the transducer 44. At tip ends of each of the vertical bar portions 45a and 45b, the support arm 42, connecting shafts 47 protruding outward are provided. Each of the connecting shafts 47 includes a round shaft 48 and restricting shafts 49, 49 extending to be symmetric with respect to a point from the round shaft 48 (see the enlarged view of the connecting shaft shown in FIG. 3). By fitting the opposite connecting shafts 47 into the connecting holes 16 in the support plates 15 provided to the inner side of the lid member 2, the support arm 42 is supported to be able to turn between the opposite support plates 15a and 15b of the lid member 2. Turning of the support arm 42 is restricted by interference between the restricting shafts 49 of the connecting shafts 47 and the fan-shaped holes 18 of the connecting holes 16.

The transducer 44 is preferably a metal plate having a mesh interior, which is mounted to a ceramic plate, which is then electrically connected to the power supply unit. Preferably, the metal plate is a rectangular plate of 7 mm in length and 8 mm in width and comprised of a Ni—Co alloy. Preferably the transducer 44 is resistant to corrosion from the spray liquid. The interior of the metal plate is comprised of a mesh material which forms the spray mist when vibrated in contact with the core and spray liquid. Preferably, the mesh size is less than 50 μm, with a hole size of less than 5 μm, with total holes on the metal plate of less than 1200 holes. However, the dimension (size) and holes are determined according to the power consumption. The metal plate is mounted on a side to a ceramic plate and electrically connected to the power supply to vibrate the transducer 44. The ceramic plate is preferably 6 mm in length and 10 mm in width.

Next, according to another embodiment of the invention, a method of assembling the liquid sprayer 1 is described. According to this embodiment, first, the power supply unit 7 is fixed into the upper portion of the support member 3. The connecting shafts 47 of the support arm 42 are fitted into the connecting holes 16 formed in the opposite support plates 15 of the lid member 2 to support the support arm 42 between the opposite side faces of the lid member 2. Next, the opposite fitting shafts 14 of the lid member 2 are inserted into the opposite fitting holes 25 in the support member 3 to connect the lid member 2 to the support member 3 so that the lid member 2 can turn. After that, an electric wire (not shown) extending from the power supply unit 7 is connected to the transducer 44 of the transducer unit 6. Then, the holding face 31 of the spray liquid storage unit 5 formed by inserting the liquid soaking holder 29 into the storage tank 28 is fitted into the holding plate 39 of the power supply unit 7 to thereby fix the spray liquid storage unit 5 into the lower portion of the support member 3. Lastly, the lid member 2 is closed onto the support member 3 and the lock pins 27 of the support member 3 are fitted into the lock holes 19 in the lid member 2 to thereby lock opening and closing of the lid member 2 with respect to the support member 3.

In the assembled liquid sprayer 1, the transducer 44 and the core 34 with which the transducer 44 is in close contact are exposed through the spray hole 8 in the lid member 2. When the electric power is supplied from the power supply unit 7 to vibrate the transducer 44, the spray liquid retained by the core 34 is turned into the mist by the vibration of the transducer 44 and sprayed outside the case main body 4 through the spray hole 8 in a direction generally perpendicular to the face of the transducer 44. Because the respective faces except the front face of the tip end portion of the core 34 in close contact with the transducer 44 are surrounded with the surrounding portion 36, it is possible to prevent the spray liquid, which has been turned into the mist by the transducer 44, from being sprayed inside the case main body 4. As it will be understood by those of skill in the art, the transducer 44 contacts the core 34 with enough distance such that the vibration of the transducer 44 draws liquid through the mesh to dissipate the spray liquid as a mist, but not so close that the core 34 restricts movement of the transducer 44.

In a preferred embodiment, the spray mist sprayed outside the main body through the spray hole is projected outside the main body in a substantially horizontal direction. In another preferred embodiment, the spray mist comprises droplets from about 1 μm to 10 μm, and more preferably droplets of less than 7 μm.

To replace the spray liquid storage unit 5, by inserting a pin (not shown) into the lock hole 19 in the lid member 2 to push the lock pin 27 inward, the locking of the lid member 2 to the support member 3 is released and the lid member 2 is turned upward with respect to the support member 3. Next, the old spray liquid storage unit 5 is detached from the holding plate 39 of the power supply unit 7 and a new spray liquid storage unit 5 is fixed to the holding plate 39. Lastly, the lid member 2 is closed onto the support member 3 and locked.

Figure 7:
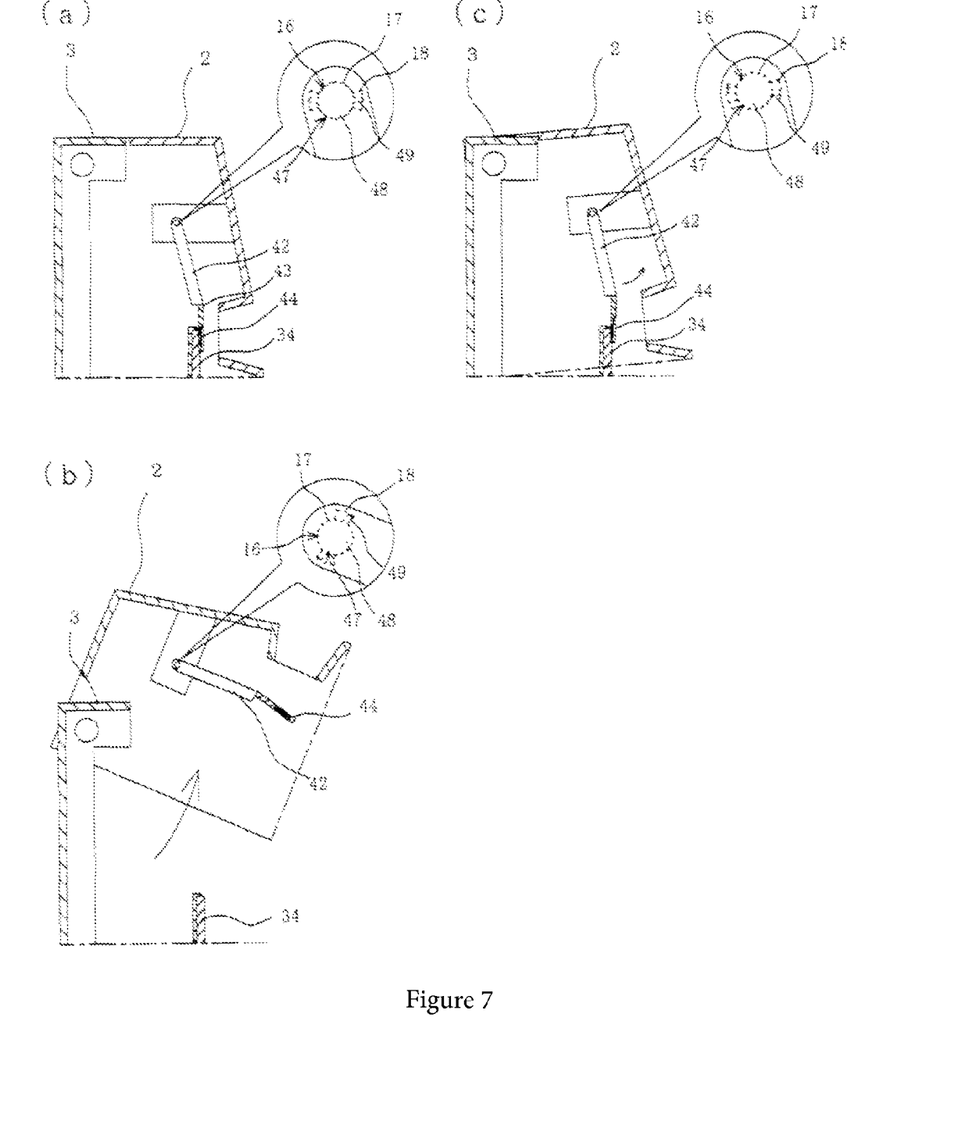
FIGS. 7A, 7B, and 7C are explanatory sectional views showing open and closed states of the lid member and the support member of the liquid sprayer shown in FIG. 1.

Next, a positional relationship between the support arm 42 and the core 34 when the lid member 2 is opened and closed with respect to the support member 3 of the liquid sprayer 1 according to the embodiment will be described based on FIGS. 7A to 7C. In each of FIGS. 7A to 7C, a lower portion of the case main body 4 and the power supply unit 7 are not shown and an enlarged view showing a relationship between the connecting shaft 47 of the support arm 42 and the connecting hole 16 of the support plates 15 is shown.

First, if the lid member 2 is completely closed onto the support member 3, an entire back face of the transducer 44 fixed to the support arm 42 comes into close contact with a front face of the core 34 as shown in FIG. 7A. At this time, the restricting shafts 49 of the connecting shafts 47 are not interfering with the fan-shaped holes 18 of the connecting holes 16 and therefore the support arm 42 can turn in a front-back direction with respect to the support plates 15. Furthermore, because the lateral bar portion 43 and the transducer 44 are positioned on the front side of the axis of turning of the support arm 42, the center of gravity of the support arm 42 is positioned on the back side of the axis of turning and a force for turning backward is always acting on the support arm 42. Therefore, the transducer 44 fixed to the support arm 42 is in close contact with and pressed against the front face of the core 34.

Next, if the lid member 2 is completely opened from the support member 3, as shown in FIG. 7B, the back face of the transducer 44 fixed to the support arm 42 is separated from the front face of the core 34. At this time, the restricting shafts 49 of the connecting shafts 47 are interfering with the fan-shaped holes 18 of the connecting holes 16. As a result, if the support arm 42 turns backward to some extent with respect to the support plates 15, the backward turning of the support arm 42 with respect to the support plates 15 is restricted.

Then, if the lid member 2 is closed onto the support member 3, as shown in FIG. 7C, a lower end of the transducer 44 fixed to the support arm 42 comes into contact with the front face of the core 34. At this time, the restricting shafts 49 of the connecting shafts 47 are not interfering with the fan-shaped holes 18 of the connecting holes 16 and, as a result, the support arm 42 can turn in the front-back direction with respect to the support plates 15. Moreover, because the lateral bar portion 43 and the transducer 44 are positioned on the front side of the axis of turning of the support arm 42, the center of gravity of the support arm 42 is positioned on the back side of the axis of turning and the force for turning backward is always acting on the support arm 42. Therefore, the lower end of the transducer 44 fixed to the support arm 42 is in contact with and pressed against the front face of the core 34.

If the lid member 2 is completely closed onto the support member 3, they come into the state shown in FIG. 7A again.

Figure 8:
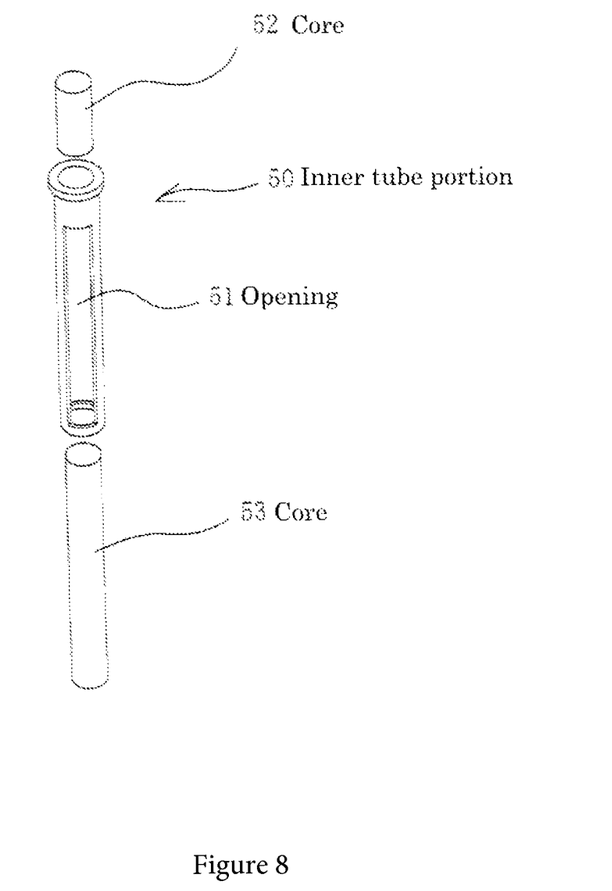
FIG. 8 is a sectional view showing a central vertical sectional view of a liquid soaking member according to another embodiment of the invention.

Another embodiment of the present invention is shown in FIG. 8. This embodiment is a variation of the inner tube portion of the liquid soaking holder described above and the same reference numerals as those in FIGS. 1 to 7C designate the same or corresponding portions in FIG. 8.

In an inner tube portion 50 according to the embodiment, as shown in FIG. 8, a large opening 51 is formed in a side face of a portion to be housed in the storage tank 28 and cores 52 and 53 having different lengths and having circular sections are housed in a hollow portion in the inner tube portion 50. The short core 52 is housed in a portion of the inner tube portion 50 to be positioned above the opening portion 30 in the storage tank 28 and the long core 53 is housed in a portion of the inner tube portion 50 to be positioned below the opening portion 30 in the storage tank 28.

In the present embodiment, the core forming the liquid soaking holder is divided into two at the position of the inner tube portion corresponding to the opening portion in the storage tank and therefore it is easy to replace only the upper end portion of the core which the transducer is in contact with and pressed against and which is relatively likely to be deformed.

The spray liquid in the invention may be fragrance, deodorant, germicide, or the like but is not limited to them. The spray liquid may be other agents which can be turned into mist by the ultrasonic vibration of the transducer.

Although the center of gravity of the support arm is positioned on the back side of the axis of turning so that the force for turning backward acts on the support arm when the transducer fixed to the support arm is brought into close contact with and pressed against the core in the method employed in First Embodiment described above, the method is not limited to it. For example, resilient bodies such as springs may be disposed at connecting portions between the support arm and the support plates to thereby always press the support arm backward.

DESCRIPTION OF REFERENCE SIGNS

1 Liquid sprayer
2 Lid member
3 Support member
4 Case main body
5 Spray liquid storage unit
6 Transducer unit
7 Power supply unit
8 Spray hole
9 Front face
10 Left side face
11 Right side face
12 Upper face
13 Lower face
14 Filling shaft
15 Support plate
16 Connecting hole
17 Circular hole
18 Fan-shaped hole
19 Lock hole
20 Back face
21 Left side face
22 Right side face
23 Upper face
24 Lower face
25 Fitting hole
26 Resilient plate
27 Lock pin
28 Storage lank
29 Liquid soaking holder
30 Opening portion
31 Holding face
32 Outer tube portion
33 Inner tube portion
34 Core
35 Connecting bridge
36 Surrounding portion
37 Box portion
38 Support piece
39 Holding plate
40 Retaining groove
41 Holding portion

42 Support arm
43 Lateral bar portion
44 Transducer
45 Vertical bar portion
46 Protecting piece
47 Connecting shaft
48 Round shaft
49 Restricting shaft
50 Inner tube portion
51 Opening
52,53 Core Although the present invention has been discussed in considerable detail with reference to certain embodiments and preferred embodiments, other embodiments are possible. Therefore, the scope of the appended claims should not be limited to the description of embodiments or preferred embodiments contained herein.

What is claimed is:

1. A liquid sprayer for dispensing a spray liquid comprising:
   (a) a main body comprising:
      a support member having a back face, an upper portion, and a lower portion;
      a power supply unit positioned on the upper portion of the support member;
      a lid member having a front face, wherein the lid member is rotatably connected to the support member to an open position, which reveals the upper portion and lower portion of the support member, and a closed position;
      a spray hole formed on the front face of the lid member; and
   (b) a spray liquid storage unit which is supported by and positioned on the lower portion of the support member, the spray liquid storage unit comprising:
      a spray liquid housed in a storage tank; and
      a core for soaking up spray liquid, wherein the spray liquid storage unit is removable from the main body when the lid member is in the open position; and
   (c) a transducer disposed inside the lid member and electrically connected to the power supply unit, such that when the lid member is in the closed position, the transducer is in close contact with and pressed against a section of the core, and the core, transducer and spray hole are substantially aligned, such that when electric power is supplied from the power supply unit to the transducer, the spray liquid retained in the core is turned into a spray mist by vibration of the transducer and sprayed outside the main body through the spray hole.

2. The liquid sprayer according to claim 1 wherein when the lid member is in the open position, the upper portion and lower portion of the support member are revealed, and wherein when the lid member is in the closed position, the transducer disposed in the lid member is disposed parallel to a front face of the core.

3. The liquid sprayer according to claim 1 wherein the lid member further comprises side faces rising from opposite sides of the front face of the lid member, and wherein a support arm is positioned between the opposite side faces of the lid member and the transducer is affixed to the support arm, which raises and lowers the transducer with the lid member and aligns the transducer with the spray hole and the core.

4. The liquid sprayer according to claim 1 wherein the support member further comprises one or more support members for supporting one or both of the power supply unit and the spray liquid storage unit.

* * * * *